(12) United States Patent
Katada et al.

(10) Patent No.: US 8,383,422 B2
(45) Date of Patent: Feb. 26, 2013

(54) IMMUNOCHROMATOGRAPHIC DEVICE

(75) Inventors: Junichi Katada, Kanagawa (JP);
Hideyuki Karaki, Minami-ashigara (JP); Takayoshi Oyamada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 713 days.

(21) Appl. No.: 12/471,805

(22) Filed: May 26, 2009

(65) Prior Publication Data
US 2009/0298050 A1 Dec. 3, 2009

(30) Foreign Application Priority Data

May 27, 2008 (JP) ................................. 2008-137923

(51) Int. Cl.
*G01N 33/558* (2006.01)

(52) U.S. Cl. ........ 436/514; 422/401; 422/413; 422/420; 422/430; 435/7.1; 435/287.1; 435/287.6; 435/287.7; 435/288.2; 435/288.5; 436/518; 436/524; 436/525; 436/807

(58) Field of Classification Search .................. 436/515, 436/518, 807, 514, 524, 525; 435/7.1, 287.1, 435/287.6, 287.7, 288.2, 288.5; 422/50, 422/401, 413, 420, 430
See application file for complete search history.

(56) References Cited

U.S. PATENT DOCUMENTS

| | | | | |
|---|---|---|---|---|
| 5,468,648 A | * | 11/1995 | Chandler | 436/518 |
| 5,482,830 A | * | 1/1996 | Bogart et al. | 435/5 |
| 5,607,863 A | * | 3/1997 | Chandler | 436/518 |
| 5,648,274 A | * | 7/1997 | Chandler | 436/514 |
| 5,726,010 A | * | 3/1998 | Clark | 435/5 |
| 5,726,013 A | * | 3/1998 | Clark | 435/5 |
| 5,846,838 A | * | 12/1998 | Chandler | 436/514 |
| 5,869,345 A | * | 2/1999 | Chandler | 436/514 |
| 5,877,028 A | * | 3/1999 | Chandler et al. | 436/514 |
| 5,879,951 A | * | 3/1999 | Sy | 436/514 |
| 5,939,252 A | * | 8/1999 | Lennon et al. | 435/4 |
| 6,017,767 A | * | 1/2000 | Chandler | 436/514 |
| 6,087,184 A | * | 7/2000 | Magginetti et al. | 436/514 |
| 6,168,956 B1 | * | 1/2001 | Chandler | 436/514 |
| 6,528,321 B1 | * | 3/2003 | Fitzgerald et al. | 436/514 |

FOREIGN PATENT DOCUMENTS

| | | |
|---|---|---|
| JP | 3496154 B2 | 6/1995 |
| JP | 11-281645 A | 10/1999 |

(Continued)

OTHER PUBLICATIONS

Japanese Office Action dated Feb. 28, 2012 issued in corresponding Japanese Patent Application No. 2008-137923 (with English translation).

*Primary Examiner* — Chris L Chin
(74) *Attorney, Agent, or Firm* — Birch, Stewart, Kolasch & Birch, LLP

(57) ABSTRACT

The present invention provides an immunochromatographic device, which contains the following (a) and (b): (a) a first device part holding a first insoluble carrier used for developing a complex formed with an analyte and a labeling substance comprising a metal labeled with a first binding substance that can bind to the analyte and capturing the analyte and the labeling substance at a reaction portion containing a second binding substance that can bind to the analyte, and (b) a second device part holding a second insoluble carrier used for developing a liquid and a third insoluble carrier used for absorbing a liquid, in such a way that the first insoluble carrier does not come into contact with the second insoluble carrier and the third insoluble carrier.

9 Claims, 2 Drawing Sheets

FOREIGN PATENT DOCUMENTS

| | | |
|---|---|---|
| JP | 2004-534944 A | 11/2004 |
| JP | 2005-55451 A | 3/2005 |
| WO | WO 95/16207 A1 | 6/1995 |
| WO | WO 02/097389 A2 | 12/2002 |

* cited by examiner

IMMUNOCHROMATOGRAPHIC DEVICE

TECHNICAL FIELD

The present invention relates to an immunochromatographic device whereby highly sensitive analysis of a sample containing an analyte can be carried out qualitatively and quantitatively.

BACKGROUND ART

Among physiologically active substances or environmental pollutants such as natural products, toxins, hormones or agricultural chemicals, numerous substances act in ultratrace amounts. Accordingly, instrumental analytical methods capable of performing highly sensitive analysis have conventionally been widely used for qualitative and quantitative measurement of these substances. However, instrumental analytical methods are poor in specificity, require excessive time for analysis including pretreatment of samples, and are troublesome in operation. Thus, instrumental analytical methods are inconvenient for the purpose of rapid and convenient measurements that have been required in recent years. Meanwhile, immunoassays are highly specific and much easier in terms of operation than instrumental analytical methods. Therefore immunoassays have gradually spread in the field of measurement of bioactive substances and environmental pollutants. However, conventional immunoassays such as enzyme immunoassays using 96-well plates and latex agglutination assays do not always provide satisfactory rapidness and convenience for measurement or detection sensitivity.

Another need expected to be enabled is as follows. Achievement of higher sensitivity of tests that currently use relatively invasive samples such as swabs and blood makes it possible to detect very small amounts of analytes contained in relatively low-invasive samples such as snot, mouth wash, and urine. Thus, less burdensome tests of patients can be realized.

In recent years, test kits using an immunochromatography method (hereinafter referred to as an immunochromatographic kit) have been used more often in examination of infections that require particularly rapid diagnosis. According to the spread of these kits, patients with infections can be identified by a rapid and convenient method, and subsequent diagnosis and therapy can be conducted immediately and accurately. For example, in an immunochromatography method using the sandwich method, a labeled second antibody (second binding substance) capable of specifically binding to an analyte (for example, an antigen), and a sample solution which may possibly contain the analyte are developed on an insoluble thin film-shaped support (for example, a glass fiber membrane, a nylon membrane, or a cellulose membrane) on which a first antibody (first binding substance) capable of specifically binding to the analyte has been immobilized in a specific region. As a result, an immune complex with the analyte is formed at the region of the insoluble thin film-shaped carrier, on which region the first antibody has been immobilized. The analyte can be measured by detecting a signal such as color development or coloring of a label. The label to be used herein may be, for example, a protein such as an enzyme, colored latex particles, metal colloids, or carbon particles.

The immunochromatography method requires neither massive facilities nor instruments for determination and measurement. Furthermore, the immunochromatography method is simple in operation and promptly gives measurement results by introducing a sample solution dropwise which may possibly contain an analyte and leaving it for approximately 5 to 10 minutes. For this reason, this technique is used widely as a convenient, rapid, and highly specific method for determination and measurement in many scenarios, such as for clinical examination in hospitals and in assays in laboratories.

Among physiologically active substances or environmental pollutants such as natural products, toxins, hormones and agricultural chemicals, many substances exert effects in ultratrace amounts that are undetectable by conventional common immunochromatography methods. Therefore, there are demands for development of rapid, convenient, and highly sensitive immunochromatography methods for such substances.

Known examples of an immunochromatography method involving signal amplification and highly sensitive assay include an enzymatic amplification method (JP Patent No. 3309977) and a silver amplification method (JP Patent Publication (Kokai) No. 2002-202307 A). There have been commercially available products for immunochromatography methods involving enzymatic amplification. JP Patent No. 3309977 describes amplification after washing. In such case, highly sensitive assay can be achieved to a greater extent than that in a conventional immunochromatography method using a metal label or colored latex particles. However, in the above case, enzymatic amplification requires time for reaction and thus measurement is time-consuming compared with the conventional cases that use labels, which is disadvantageous.

In the case of immunochromatography involving silver amplification, the background level derived from metal label particles must be reduced in order to obtain a favorable signal/noise (S/N) ratio. Therefore, it is necessary to carry out washing in order to increase the final detection sensitivity. In a system to which a membrane for washing is previously provided, an antigen solution accidentally flows in the direction of a second insoluble carrier or a third insoluble carrier upon development of the antigen solution, resulting in loss of labeled antibodies, leading to a decrease in sensitivity. In addition, labels that have accidentally flowed in the direction of a second insoluble carrier cause an increase in the background level. Eventually, the S/N ratio derived from the detection level and the background level decreases and thus the detection sensitivity decreases, which is problematic.

DISCLOSURE OF THE INVENTION

It is an object of the present invention to provide an immunochromatographic device for immunochromatography comprising developing a complex formed with an analyte and a labeling substance comprising a metal labeled with a first binding substance that can bind to the analyte on a first insoluble carrier, capturing the analyte and the labeling substance at a reaction portion on an insoluble carrier containing a second binding substance that can bind to the analyte, and detecting the analyte, whereby it is possible to solve the problem of the analyte (antigen solution) accidentally flowing in the direction of a second insoluble carrier used for developing a wash solution and a third insoluble carrier used for absorbing a wash solution when the antigen solution is developed.

As a result of intensive studies in order to achieve the above object, the present inventors have discovered the fact that it is possible to solve the problem of an antigen solution accidentally flowing in the direction of a second insoluble carrier used for developing a wash solution and a third insoluble carrier used for absorbing a wash solution by constructing a device as follows. Namely, the problem can be solved by the steps of: developing a complex formed with an analyte (antigen solution) and a labeling substance comprising a metal labeled with a first binding substance that can bind to the analyte on a first insoluble carrier used for capturing the analyte and the labeling substance at a reaction portion containing a second binding substance that can bind to the analyte; and then attaching a second insoluble carrier used for developing a wash solution and a third insoluble carrier used for absorbing a wash solution to the first insoluble carrier. The above findings have led to the completion of the present invention.

The present invention provides an immunochromatographic device, which contains the following (a) and (b):

(a) a first device part holding a first insoluble carrier used for developing a complex formed with an analyte and a labeling substance comprising a metal labeled with a first binding substance that can bind to the analyte and capturing the analyte and the labeling substance at a reaction portion containing a second binding substance that can bind to the analyte, and (b) a second device part holding a second insoluble carrier used for developing a liquid and a third insoluble carrier used for absorbing a liquid, in such a way that the first insoluble carrier does not come into contact with the second insoluble carrier and the third insoluble carrier.

Preferably, the immunochromatographic device according to the present invention further comprises a positioning mechanism whereby the positions of the first device part and the second device part can be positioned in a manner such that the first insoluble carrier comes into contact or does not come into contact with the second insoluble carrier and the third insoluble carrier.

Preferably, the second device part has pores for dropwise introduction of an analyte.

Preferably, the first device part has a liquid storage pot.

Preferably, the immunochromatographic device according to the present invention has a structure in which one end of the second insoluble carrier is immersed in the liquid storage pot when the first device part and the second device part are positioned in a manner such that the first insoluble carrier comes into contact with the second insoluble carrier and the third insoluble carrier.

Preferably, the liquid storage pot is previously loaded with a liquid.

Preferably, the immunochromatographic device according to the present invention has a structure in which the first device part has two liquid storage pots and one end of the second insoluble carrier is split in two ways, provided that the two split ends are separately immersed in the two liquid storage pots when the first device part and the second device part are positioned in a manner such that the first insoluble carrier comes into contact with the second insoluble carrier and the third insoluble carrier.

Preferably, the first device part has a first liquid storage pot, the second device part has two second liquid storage pots positioned to face the first liquid pot, and a silver-containing compound and a reducing agent for silver ion are separately and previously loaded into the two second liquid storage pots. An example of this embodiment is shown in FIG. 3.

Preferably, the first device part has a first liquid storage pot, the second device part has two second liquid storage pots positioned to face the first liquid pot, and the first liquid storage pot has inside a Y- or V-shaped projecting pin facing the second liquid storage pots, provided that the external wall of each second liquid storage pot is pierced with the projecting pin and thus liquids inside the two second liquid storage pots are transferred via the projecting pin into the first liquid storage pot, followed by mixing, when the first device part and the second device part are positioned in a manner such that the first insoluble carrier comes into contact with the second insoluble carrier and the third insoluble carrier. An example of this embodiment is shown in FIG. 4.

Preferably, the first insoluble carrier is a porous carrier.

The present invention further provides an immunochromatography method comprising: developing a complex formed with an analyte and a labeling substance comprising a metal labeled with a first labeling substance that can bind to the analyte on a first insoluble carrier; capturing the analyte and the labeling substance at a reaction portion on an insoluble carrier containing a second binding substance that can bind to the analyte; and detecting the analyte; which comprises the following steps (1) to (4) of:

(1): developing the analyte;

(2): allowing the second insoluble carrier used for developing wash solution and the third insoluble carrier used for absorbing a development solution to adhere to the first insoluble carrier;

(3): washing away substances other than labeling substance captured as a result of specific binding at a reaction portion on the first insoluble carrier by feeding a wash solution; and (4): carrying out sensitization with the use of an amplification solution comprising a silver-containing compound and a reducing agent for silver ion; provided that the steps (1) to (4) are carried out in the above order.

Preferably, the labeling substance is a metal colloid.

Preferably, the metal colloid is a gold colloid.

Preferably, the amplification solution contains iron (II) ions.

The immunochromatographic device of the present invention is a device in which an analyte (antigen solution) is first developed on an immunochromatographic strip, following which a second insoluble carrier used for developing a wash solution and a third insoluble carrier used for absorbing a wash solution are attached to the immunochromatographic strip. Due to such configuration, in the case of the immunochromatographic device of the present invention, an analyte (antigen solution) does not accidentally flow in the direction of to a second insoluble carrier or a third insoluble carrier when it is developed. Thus, it is possible to prevent the signal reduction due to loss of antigens and the background noise increase due to flow of a labeling substance in the direction of a second insoluble carrier. Eventually, high-sensitive detection can be carried out.

Figure 1:
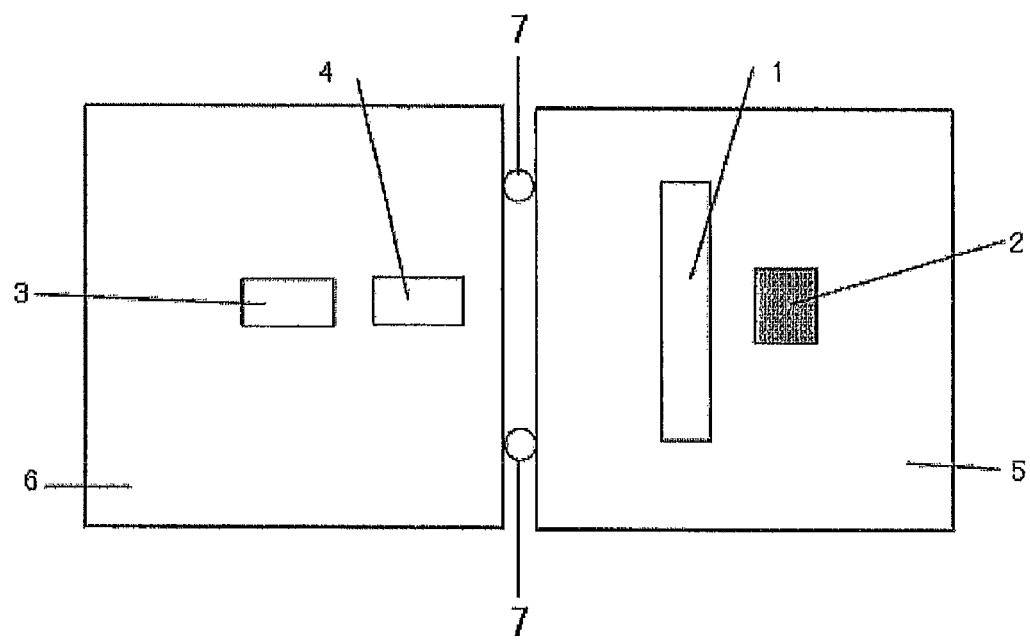
FIG. 1 shows an example of the immunochromatographic device of the present invention.

In figures, first insoluble carrier (1) (immunochromatographic strip), liquid storage pot (2), second insoluble carrier (3), third insoluble carrier (4), first device part (5), second device part (6), positioning mechanism (7), second liquid storage pot (8) and Y-shaped projecting pin (9) are shown.

PREFERRED EMBODIMENT OF THE INVENTION

1. Immunochromatography

In general, immunochromatography is a method for determining and/or measuring an analyte, simply, rapidly and specifically, by the following means. That is to say, a chromatographic carrier having at least one reaction zone comprising an immobilizing reagent (an antibody, an antigen, etc.) capable of binding to an analyte is used as an immobilization phase. On this chromatographic carrier, a dispersed liquid formed by dispersion of a labeling substance used in detection, which is modified by a reagent capable of binding to an analytical target, is used as a mobile phase, and the mobile phase is moved in the chromatographic carrier in a chromatographic manner. At the same time, the aforementioned analytical target specifically binds to the labeling substance used in detection, and they reach the aforementioned reaction zone. At the aforementioned reaction zone, a complex of the aforementioned analytical target and the aforementioned labeling substance used in detection specifically binds to the aforementioned immobilizing reagent. Utilizing the phenomenon whereby the labeling substance used in detection is concentrated in the immobilizing reagent portion only when the analytical target exists in an analyzed solution, the presence of a product to be detected in the analyzed solution is qualitatively and quantitatively analyzed by visual observation or using an adequate apparatus.

The apparatus used to perform such an immunochromatography method in the present invention may comprise a compound containing silver and a reducing agent for silver ion. A signal is amplified by an amplification reaction using, as a core, a complex of the aforementioned analytical target and the aforementioned labeling substance used in detection binding to the aforementioned immobilizing reagent, so as to achieve high sensitivity. According to the present invention, a rapid and highly sensitive immunochromatography can be carried out.

2. Test Sample

The type of a test sample that can be analyzed by the immunochromatography of the present invention is not particularly limited, as long as it may comprise an analytical target. Examples of such a test sample include biological samples such as the body fluids of animals (particularly, a human) (e.g. blood, serum, plasma, spinal fluid, lacrimal fluid, sweat, urine, pus, runny nose, and sputum), excrements (e.g. feces), organs, tissues, mucous membranes, skin, a swab and a rinsed solution that are considered to contain them, and animals or plants themselves or the dried products thereof.

3. Pre-Treatment of Test Sample

In the immunochromatography of the present invention, the aforementioned test sample can directly be used. Otherwise, the aforementioned test sample can also be used in the form of an extract obtained by extracting it with a suitable extraction solvent, or in the form of a diluted solution obtained by diluting the aforementioned extract using a suitable diluent, or in the form of a concentrate obtained by concentrating the aforementioned extract by a suitable method. As the aforementioned extraction solvent, solvents used in common immunological analysis methods (e.g. water, a normal saline solution, a buffer, etc.) or water-miscible organic solvents that enable a direct antigen-antibody reaction as a result of dilution with the aforementioned solvents can be used.

4. Structure

The type of "the first insoluble carrier used for developing a complex formed with an analyte and a labeling substance comprising a metal labeled with a first binding substance (for example, a first antibody) that can bind to the analyte and capturing the analyte and the labeling substance at a reaction portion containing a second binding substance (for example, a second antibody) that can bind to the analyte" in the immunochromatographic device of the present invention is not particularly limited, as long as it is an immunochromatographic strip that can be used in a common immunochromatography.

In an immunochromatographic strip of the present invention, a sample-adding pad, a labeling substance-retaining pad (e.g. a gold colloid antibody-retaining pad), a chromatographic carrier (e.g. an antibody-immobilized membrane), and an absorbent pad are disposed in this order on an adhesive sheet from the upstream to the downstream of a development direction.

The chromatographic carrier has a capturing site and a detection zone (which is also referred to as a "detection portion") that is a region on which an antibody or an antigen specifically binding to an analytical target is immobilized. The chromatographic carrier also has a control zone (which is also referred to as a "control portion") that is a region on which a control antibody or antigen is immobilized, as desired.

The labeling substance-retaining pad can be produced by preparing a suspension containing a labeling substance, applying the suspension to a suitable absorbent pad (e.g. a glass fiber pad), and then drying it.

As the sample-adding pad, a glass fiber pad can be used, for example.

4-1. Labeling Substance Used in Detection

As a label used in detection for preparing a labeling substance, any label which can be visually observed or can be detected by a reaction, can be used. Examples thereof include metal fine particles, colored latex particles and enzymes, which are used in the conventional immunochromatography.

In the present invention, metal colloid, metal sulfide, metal alloy or polymer particle label containing metal, can be used as a label for detection. The mean particle diameter of a carrier particle (or colloid) is preferably between 0.02 and 10 µm. Examples thereof include a gold colloid, a silver colloid, a platinum colloid, an iron colloid, an aluminum hydroxide colloid, and a complex colloid thereof. Preferred examples include a gold colloid, a silver colloid, a platinum colloid, and a complex colloid thereof. A gold colloid and a silver colloid are particularly preferable in that the gold colloid exhibits a red color and the silver colloid exhibits a yellow color when they have an appropriate particle diameter. The mean particle diameter of a metal colloid is preferably between approximately 1 nm and 500 nm, more preferably between 1 nm and 50 nm.

The metal colloid can be bound to a first binding substance (for example, a first antibody) according to conventionally known methods (e.g. The Journal of Histochemistry and Cytochemistry, Vol. 30, No. 7, pp. 691-696 (1982)). That is to say, a metal colloid is mixed with a first binding substance in a suitable buffer at room temperature for 5 or more minutes. After completion of the reaction, a precipitate obtained by centrifugation is dispersed in a solution containing a dispersant such as polyethylene glycol to obtain a metal colloid-labeled binding substance of interest. When gold colloid particles are used as the metal colloid, commercially available gold colloid particles may be used. Alternatively, such gold colloid particles may be prepared by a common method, for example, by a method of reducing chlorauric acid with sodium citrate (Nature Phys. Sci., vol. 241, 20 (1973), etc.).

According to the present invention, in an immunochromatography using, as a labeling substance used in detection, a metal colloid label, a metallic sulfide label, a metal alloy label, or a metal-containing polymer particle label, the signal from the aforementioned metallic label can be amplified. Specifically, after formation of a complex of the analytical target and the labeling substance used in detection, silver ions supplied from a compound containing silver such as an organic silver salt are allowed to come into contact with a reducing agent for silver ions, so that the silver ions are reduced with the reducing agent to form silver particles. Thus, the silver particles are deposited on the aforementioned metallic labeling substance as a core, so that the metallic labeling substance is amplified to enable the high-sensitivity analysis of the analytical target. Accordingly, the conventionally known immunochromatography can directly be applied to the immunochromatography of the present invention with the exception that a reaction of precipitating silver particles generated as a result of reduction of silver ions with the reducing agent on the labeling substance of an immune complex is carried out, so as to analyze the thus amplified signal.

4-2. Binding Substance

In the present invention, the type of the first binding substance may be any substance so long as it has an affinity against the analyte. Examples of the first binding substance may include an antibody. In the immunochromatography of the present invention, the type of an antibody having specificity for an analytical target is not particularly limited. Examples of an antibody used herein include an antiserum prepared from the serum of an animal immunized with the analytical target, an immunoglobulin fraction purified from the antiserum, a monoclonal antibody obtained by cell fusion using the splenic cells of the animal immunized with the analytical target, and the fragments thereof (for example, F(ab')2, Fab, Fab' or Fv). Such an antibody may be prepared by a common method.

4-3. First Insoluble Carrier

The first insoluble carrier is a chromatographic carrier which has at least one reaction portion containing a second binding substance (for example, a second antibody) that can bind to the analyte. This chromatographic carrier is preferably a porous carrier. It is particularly preferably a nitrocellulose membrane, a cellulose membrane, an acetyl cellulose membrane, a polysulfone membrane, a polyether sulfone membrane, a nylon membrane, glass fibers, a nonwoven fabric, a cloth, threads or the like.

Usually, a second binding substance (for example, second antibody) is immobilized on a part of the chromatographic carrier to form a detection zone. The second binding substance may be directly immobilized on a part of the chromatographic carrier via a physical or chemical bond. Alternatively, the second binding substance may be bound physically or chemically to fine particles such as latex particles, and thereafter, the fine particles are immobilized on a part of the chromatographic carrier by trapping them thereon. After immobilization of the second binding substance on the chromatographic carrier, the chromatographic carrier may preferably be subjected to a treatment for preventing unspecific adsorption, such as a treatment using an inert protein, and it may be then used.

Examples of a material for the sample-adding pad include, but are not limited to, those having uniform characteristics, such as a cellulose filter paper, glass fibers, polyurethane, polyacetate, cellulose acetate, nylon, and a cotton cloth. A sample-adding portion not only acts to receive a sample containing the added analytical target, but also acts to filter off insoluble particles, etc. contained in the sample. Moreover, in order to prevent a decrease in analysis precision occurring during the analysis due to unspecific adsorption of the analytical target contained in the sample on the material of the sample-adding portion, the material constituting the sample-adding portion may be subjected to a treatment for preventing unspecific adsorption before use.

Examples of a material for the labeling substance-retaining pad include a cellulose filter paper, glass fibers, and a nonwoven fabric. Such a labeling substance-retaining pad is prepared by impregnating the pad with a predetermined amount of the labeling substance used in detection as prepared above and then drying it.

The absorbent pad is a portion for physically absorbing the added sample as a result of the chromatographic migration and for absorbing and removing an unreacted labeling substance, etc. that is not immobilized on the detection portion of the chromatographic carrier. Examples of a material for the absorbent pad include water-absorbing materials such as a cellulose filter paper, a nonwoven fabric, a cloth or cellulose acetate. The chromatographic speed after the chromatographic leading end of the added sample has reached the absorbing portion varies depending on the material and size of the absorbent material, etc. Thus, a speed adequate for the measurement of the analytical target can be determined by selection of the material and size of the absorbent material.

4-4. Second Insoluble Carrier for Developing a Wash Solution

The second insoluble carrier for developing a wash solution used in the present invention may be any carrier, so long as a wash solution can be added. Examples thereof include a glass fiber pad, a cellulose membrane, and a nitrocellulose membrane.

4-5. Third Insoluble Carrier for Absorbing a Wash Solution

The third insoluble carrier (water-absorbing pad) for absorbing a wash solution used in the present invention may be any carrier, so long as it can absorb water. Examples thereof include cellulose, nitrocellulose, glass fibers, or a mixed material thereof.

5. Immunological Test Method

Hereinafter, a sandwich method which is specific embodiments of the immunochromatography of the present invention, will be described. In the sandwich method, an analytical target can be analyzed by the following procedures, for example, but the procedures are not particularly limited thereto. First, a primary antibody and a secondary antibody having specificity for an analytical target (an antigen) have previously been prepared by the aforementioned method. In addition, the primary antibody has previously been labeled. The second antibody is immobilized on a suitable insoluble thin-membrane support (e.g. a nitrocellulose membrane, a glass fiber membrane, a nylon membrane, a cellulose membrane, etc.), and it is then allowed to come into contact with a test sample (or an extract thereof) that is likely to contain the analytical target (the antigen). If the analytical target actually exists in the test sample, an antigen-antibody reaction occurs. This antigen-antibody reaction can be carried out in the same manner as that of an ordinary antigen-antibody reaction. At the same time of the antigen-antibody reaction or after completion of the reaction, an excessive amount of the labeled primary antibody is further allowed to come into contact with the resultant. If the analytical target exists in the test sample, an immune complex of the immobilized second antibody, the analytical target (antigen) and the labeled primary antibody is formed.

In the sandwich method, after completion of the reaction of the immobilized second antibody, the analytical target (antigen) and the primary antibody, the labeled primary antibody that has not formed the aforementioned immune complex is removed. Subsequently, a metal ion and a reducing agent are supplied to a region of the insoluble thin-membrane support, on which the second antibody has been immobilized, for example, so that a signal from the labeling substance of the labeled primary antibody that has formed the aforementioned immune complex is amplified.

6. Washing 6.1 Wash Solution

According to the present invention, a PBS buffer containing 1% BSA may be used as a wash solution. However, any solution can be used as a wash solution as long as it can be used for washing a labeling substance remaining on a membrane (in a non-specific manner) as a result of a non-specific binding reaction. It is also possible to use wash solution with a pH that has been adjusted to improve washing effects, or a wash solution containing a surfactant component, a protein such as BSA or a high molecular compound such as polyethylene glycol.

Upon development of such a wash solution, a labeling substance remaining in a non-specific manner is washed with the wash solution. Thus, the wash solution is allowed to contain a labeled substance when being developed. A wash solution before being developed contains no labeling substance such that washing effects can be improved.

6-2. Development of a Wash Solution, and the Development Direction

A wash solution is added to an immunochromatographic strip on which a specimen solution has been developed such that a labeling substance remaining in the immunochromatographic strip as a result of a non-specific binding reaction is washed with the wash solution. Examples of a method for feeding a wash solution that can be used include: a method wherein a specimen solution is developed and then a wash solution is added to a portion to which the sample has been added dropwise; a method wherein a wash solution addition pad and a water absorbent pad, which are used for feeding a wash solution, are attached to a strip and then the wash solution is added to the wash solution addition pad so as to be fed in the direction of the water absorbent pad; a method wherein a wash solution addition portion is prepared on a strip, a specimen solution is developed on the strip, and then the wash solution is added to the wash solution addition portion; and a method wherein a specimen solution is developed on a strip and then a wash solution addition pad and a water absorbent pad, which are used for feeding a wash solution, are attached to the strip.

Herein, the direction of development of an analyte is defined as the direction of a line extending from a sample addition pad to an absorbent pad. The direction of development of the wash solution is defined as the direction of a line extending from a wash solution addition pad to a water absorbent pad, provided that both pads are used for feeding a wash solution.

An angle formed by a line extending in the direction of development of an analyte solution and a line extending in the direction of development of a wash solution is not particularly limited. It can be 0° to 180°.

7. Amplification Solution

An amplification solution that can be used in the present invention is what is called a developing solution as described in publications common in the field of photographic chemistry (e.g. "*Kaitei Shashin kagaku no kiso, Ginen shashin hen* (Revised Basic Photographic Engineering, silver salt photography)," (the Society of Photographic Science and Technology of Japan, Colona Publishing Co., Ltd.); "*Shashin no kagaku* (Photographic Chemistry)," (Akira Sasai, Shashin Kogyo Shuppan); "*Saishin Shoho Handbook* (Latest Formulation Handbook)," (Shinichi Kikuchi et al., Amiko Shuppan); etc.).

In the present invention, any type of amplification solution can be used, as long as it is what is called a physical developing solution, which comprises silver ions, and such silver ions in the solution act as a core of development and reduction is carried out using a metal colloid as a center.

8. Compound that Contains Silver

The silver-containing compound used in the present invention may be an organic silver salt, an inorganic silver salt, or a silver complex.

The organic silver salt used in the present invention is an organic compound containing a reducible silver ion. Any one of an organic silver salt, an inorganic silver salt and a silver complex may be used as a compound containing a reducible silver ion in the present invention. For example, a silver nitrate, a silver acetate, a silver lactate, a silver butyrate, etc. have been known.

In addition, such a compound may be a silver salt or a coordination compound that forms a metallic silver relatively stable for light, when it is heated to 50° C. in the presence of a reducing agent.

The organic silver salt used in the present invention may be a compound selected from the silver salts of an azole compound and the silver salts of a mercapto compound. Such an azole compound is preferably a nitrogen-containing heterocyclic compound, and more preferably a triazole compound and a tetrazole compound. The mercapto compound is a compound having at least one mercapto group or thione group in the molecule thereof.

The silver salt of the nitrogen-containing heterocyclic compound of the present invention is preferably the silver salt of a compound having an imino group. Typical compounds include, but are not limited to, the silver salt of 1,2,4-triazole, the silver salt of benzotriazole or a derivative thereof (for example, a methylbenzotriazole silver salt and a 5-chlorobenzotriazole silver salt), a 1H-tetrazole compound such as phenylmercaptotetrazole described in U.S. Pat. No. 4,220,709, and imidazole or an imidazole derivative described in U.S. Pat. No. 4,260,677. Among these types of silver salts, a benzotriazole derivative silver salt or a mixture of two or more silver salts is particularly preferable.

The silver salt of the nitrogen-containing heterocyclic compound used in the present invention is most preferably the silver salt of a benzotriazole derivative.

The compound having a mercapto group or a thione group of the present invention is preferably a heterocyclic compound having 5 or 6 atoms. In this case, at least one atom in the ring is a nitrogen atom, and other atoms are carbon, oxygen, or sulfur atoms. Examples of such a heterocyclic compound include triazoles, oxazoles, thiazoles, thiazolines, imidazoles, diazoles, pyridines, and triazines. However, examples are not limited thereto.

Typical examples of the silver salt of the compound having a mercapto group or a thione group include, but are not limited to, the silver salt of 3-mercapto-4-phenyl-1,2,4-triazole, the silver salt of 2-mercapto-benzimidazole, the silver salt of 2-mercapto-5-aminothiazole, the silver salt of mercaptotriazine, the silver salt of 2-mercaptobenzoxazole, and the silver salt of compounds described in U.S. Pat. No. 4,123,274.

As such a compound having a mercapto group or a thione group of the present invention, a compound that does not contain a hetero ring may also be used. As such a mercapto or thione derivative that does not contain a hetero ring, an aliphatic or aromatic hydrocarbon compound having total 10 or more carbon atoms is preferable.

Among such mercapto or thione derivatives that do no contain a hetero ring, useful compounds include, but are not limited to, the silver salt of thioglycolic acid (for example, the silver salt of S-alkylthioglycolic acid having an alkyl group containing 12 to 22 carbon atoms) and the silver salt of dithiocarboxylic acid (for example, the silver salt of dithioacetic acid and the silver salt of thioamide).

An organic compound having the silver salt of carboxylic acid is also preferably used. It is straight-chain carboxylic acid, for example. Specifically, carboxylic acid containing 6 to 22 carbon atoms is preferably used. In addition, the silver salt of aromatic carboxylic acid is also preferable. Examples of such aromatic carboxylic acid and other carboxylic acids include, but are not limited to, substituted or unsubstituted silver benzoate (for example, silver 3,5-dihydroxybenzoate, silver o-methylbenzoate, silver m-methylbenzoate, silver p-methylbenzoate, silver 2,4-dichlorobenzoate, silver acetamide benzoate and silver p-phenylbenzoate), silver tannate, silver phthalate, silver terephthalate, silver salicylate, silver phenylacetate, and silver pyromellitate.

In the present invention, aliphatic acid silver containing a thioether group as described in U.S. Pat. No. 3,330,663 can also be preferably used. A soluble silver carboxylate having a hydrocarbon chain containing an ether bond or a thioether bond, or a soluble silver carboxylate having a sterically hindered substituent on an α-position (of the hydrocarbon group) or an ortho-position (of the aromatic group) can also be used. These silver carboxylates have an improved solubility in a coating solvent, which provides a coating material having little light scattering.

Such silver carboxylates are described in U.S. Pat. No. 5,491,059. All of the mixtures of the silver salts described therein can be used in the invention, as necessary.

The silver salt of sulfonate as described in U.S. Pat. No. 4,504,575 can also be used in the embodiment of the present invention.

Further, for example, the silver salt of acetylene described in U.S. Pat. Nos. 4,761,361 and 4,775,613 can also be used in the present invention. It can be provided as a core-shell type silver salt as described in U.S. Pat. No. 6,355,408. Such silver salt is composed of a core consisting of one or more silver salts and a shell consisting of one or more different silver salts.

In the present invention, another product useful as a non-photosensitive silver source is a silver dimer composite consisting of two different types of silver salts described in U.S. Pat. No. 6,472,131. Such a non-photosensitive silver dimer composite consists of two different types of silver salts. When the aforementioned two types of silver salts include a linear saturated hydrocarbon group as a silver ligand, a difference in the numbers of carbon atoms of the ligands is 6 or greater.

The organic silver salt is contained as silver generally in an amount of 0.001 to 0.2 mol/m$^2$, and preferably 0.01 to 0.05 mol/m$^2$, in terms of the silver amount.

The inorganic silver salt or the silver complex used in the present invention is a compound containing a reducible silver ion. Preferably, such an inorganic silver salt or a silver complex is an inorganic silver salt or a silver complex, which forms metallic silver relatively stable for light, when the salt or complex is heated to 50° C. or higher in the presence of a reducing agent.

Examples of the inorganic silver salt used in the present invention include: a silver halide (such as silver chloride, silver bromide, silver chlorobromide, silver iodide, silver chloroiodide, silver chloroiodobromide, and silver iodobromide); the silver salt of a silver thiosulfate (e.g. a sodium salt, a potassium salt, an ammonium salt, etc.); the silver salt of a silver thiocyanate (e.g. a sodium salt, a potassium salt, an ammonium salt, etc.); and the silver salt of a silver sulfite (e.g. a sodium salt, a potassium salt, an ammonium salt, etc.).

The inorganic silver salt used in the present invention is preferably a silver halide.

A method for forming the particles of the silver halide used in the invention is well known in the photographic industry. For example, methods described in Research Disclosure No. 17029, June 1978, and U.S. Pat. No. 3,700,458 may be used. Specifically, such a silver halide may be prepared by adding a silver-supplying compound (for example, a silver nitrate) and a halogen-supplying compound to a solution of a gelatin or other polymers.

The particle size of the silver halide is preferably very small in order to reduce examination noise. Specifically, the size is preferably 0.20 μm or less, more preferably 0.10 μm or less, and even more preferably in the range of nanoparticles. The term "particle size" is used herein to mean a diameter of a circular image having the same area as the projected area of the silver halide particle (the projected area of the main plane in the case of a tabular particle).

A silver thiosulfate, a silver thiocyanate, and a silver sulfite can also be prepared in the same manner as the formation of silver halide particles, by mixing a silver-supplying compound (such as a silver nitrate) with a thiosulfate (e.g. a sodium salt, a potassium salt, an ammonium salt, etc.), a thiocyanate (e.g. a sodium salt, a potassium salt, an ammonium salt, etc.), and a sulfite (e.g. a sodium salt, a potassium salt, an ammonium salt, etc.), respectively.

In general, if the concentration of silver ion in the amplification solution is too high, such silver ion is reduced in the amplification solution. In order to prevent such a phenomenon, a complexing agent may be used to cause the silver ion to form a complex. As such a complexing agent, amino acids such as glycine and histidine, heterocyclic bases, imidazole, benzimidazole, pyrazole, purine, pyridine, aminopyridine, nicotinamide, quinoline, and other similar aromatic heterocyclic compounds have been known. These compounds are described in E.P. Patent No. 0293947, for example. Further, as a complex salt-forming agent, thiosulfate, thiocyanate, and the like can also be used. Specific examples of the silver complex used in the present invention include a complex of a thiosulfate and a silver ion, a complex of a thiocyanate and a silver ion, a composite silver complex thereof, a complex of a sugar thione derivative and a silver ion, a complex of a cyclic imide compound (e.g. uracil, urazole, 5-methyluracil, barbituric acid, etc.) and a silver ion, and a complex of a 1,1-bissulfonylalkane and a silver ion. A preferred silver complex used in the invention is a complex of a cyclic imide compound (e.g. uracil, urazole, 5-methyluracil, barbituric acid, etc.) and a silver ion.

The silver complex used in the present invention may be prepared by a generally-known salt forming reaction. For example, the silver complex may be prepared by mixing in water or a water-miscible solvent a water-soluble silver supplier (such as a silver nitrate) with a ligand compound corresponding to the silver complex. The prepared silver complex can be used, after salts generated as by-products have been removed by a known desalting method such as dialysis or ultrafiltration.

The inorganic silver salt or the silver complex is contained as silver generally in an amount of 0.001 to 0.2 mol/m², and preferably 0.01 to 0.05 mol/m², in terms of the silver amount.

When an inorganic silver salt or a silver complex is used, a solvent for them is preferably used. The solvent used in the present invention is preferably a compound used as a ligand for forming a silver complex described in the above paragraphs for the "silver complex." Examples of such a compound used as a solvent in the present invention include a thiosulfate, a thiocyanate, a sugar thione derivative, a cyclic imide compound, and a 1,1-bissulfonylalkane. The solvent used in the present invention is more preferably a cyclic imide compound such as uracil, urazole, 5-methyluracil, or barbituric acid. The solvent used in the present invention is preferably used at a molar ratio of 0.1 to 10 moles with respect to silver ions.

9. Reducing Agent Used for Silver Ion

As a reducing agent used for silver ion, either inorganic or organic materials capable of reducing silver(I) ion to silver, or the mixtures thereof, may be used.

As an inorganic reducing agent, reducible metal salts and reducible metal complex salts whose valence can be changed with metal ions such as $Fe^{2+}$, $V^{2+}$ or $Ti^{3+}$ have been known. These salts can be used in the present invention. When such an inorganic reducing agent is used, it is necessary to form a complex with the oxidized ion or reduce it, so as to remove or detoxify the oxidized ion. For example, in a system using $Fe^{+2}$ as a reducing agent, citric acid or EDTA is used to form a complex with $Fe^{3+}$ as an oxide, so as to detoxify it.

In the present system, such an inorganic reducing agent is preferably used. The metal salt of $Fe^{2+}$ is more preferable.

Developing agents used for wet-process silver halide photographic-sensitized materials (for example, methyl gallate, hydroquinone, substituted hydroquinone, 3-pyrazolidones, p-aminophenols, p-phenylenediamines, hindered phenols, amidoximes, azines, catechols, pyrogallols, ascorbic acid (or derivatives thereof), and leuco dyes), or other materials known to those skilled in the art (see, for example, U.S. Pat. No. 6,020,117 (Bauer et al.)) may be used in the present invention.

The term "ascorbic acid reducing agent" means a complex of ascorbic acid and a derivative thereof. Ascorbic acid reducing agents are described in many publications, as described below, including, for example, U.S. Pat. No. 5,236,816 (Purol et al.) and publications cited therein.

The reducing agent used in the present invention is preferably an ascorbic acid reducing agent. Useful ascorbic acid reducing agents include ascorbic acid, an analogue thereof, an isomer thereof, and a derivative thereof. Examples of such compounds include the following compounds. However, examples are not limited thereto.

Examples of such compounds include D- or L-ascorbic acid and a sugar derivative thereof (for example, γ-lactoascorbic acid, glucoascorbic acid, fucoascorbic acid, glucoheptoascorbic acid, and maltoascorbic acid), sodium ascorbate, potassium ascorbate, isoascorbic acid (or L-erythroascorbic acid), and a salt thereof (for example, an alkali metal salt, an ammonium salt, or salts known in the art), and endiol-type ascorbic acid, enaminol-type ascorbic acid and thioenol-type ascorbic acid such as compounds described in U.S. Pat. No. 5,498,511, EP-A-0585,792, EP-A 0573700, EP-A 0588408, U.S. Pat. Nos. 5,089,819, 5,278,035, 5,384,232 and 5,376, 510, JP 7-56286, U.S. Pat. No. 2,688,549, and Research Disclosure 37152 (March, 1995).

Among these compounds, D-, L-, and D,L-ascorbic acid (and an alkali metal salt thereof), and isoascorbic acid (and an alkali metal salt thereof) are preferable. Moreover, a sodium salt is a preferred salt thereof. If necessary, a mixture of these reducing agents may also be used.

A hindered phenol may be preferably used singly or in combination with one or more gradation-hardening reducing agents and/or contrast enhancers.

A hindered phenol is a compound having only one hydroxyl group on a benzene ring and also having at least one substituent at the ortho-position relative to the hydroxyl group. The hindered phenol reducing agent may have plural hydroxyl groups, as long as the hydroxyl groups are located on different benzene rings.

Examples of the hindered phenol reducing agent include binaphthols (that is, dihydroxybinaphthols), biphenols (that is, dihydroxybiphenols), bis(hydroxynaphthyl)methanes, bis(hydroxyphenyl)methanes (that is, bisphenols), hindered phenols, and hindered naphthols, each of which may be substituted.

Typical binaphthols include, but are not limited to, 1,1'-bi-2-naphthol, 1,1'-bi-4-methyl-2-naphthol, and compounds described in U.S. Pat. Nos. 3,094,417 and 5,262,295.

Typical biphenols include, but are not limited to, 2-(2-hydroxy-3-t-butyl-5-methylphenyl)-4-methyl-6-n-hexylphenol, 4,4'-dihydroxy-3,3',5,5'-tetra-t-butylbiphenyl, 4,4'-dihydroxy-3,3',5,5'-tetramethylbiphenyl, and compounds described in U.S. Pat. No. 5,262,295.

Typical bis(hydroxynaphthyl)methanes include, but are not limited to, 4,4'-methylenebis(2-methyl-1-naphthol) and compounds described in U.S. Pat. No. 5,262,295.

Typical bis(hydroxyphenyl)methanes include, but are not limited to, bis(2-hydroxy-3-t-butyl-5-methylphenyl)methane (CAO-5), 1,1'-bis(2-hydroxy-3,5-dimethylphenyl)-3,5,5-trimethyl hexane (NONOX or PERMANAX WSO), 1,1'-bis(3, 5-di-t-butyl-4-hydroxyphenyl)methane, 2,2'-bis(4-hydroxy-3-methylphenyl) propane, 4,4'-ethylidene-bis(2-t-butyl-6-methylphenol), 2,2'-isobutylidene-bis(4,6-dimethylphenol) (LOWINOX 221B46), 2,2'-bis(3,5-dimethyl-4-hydroxyphenyl)propane, and compounds described in U.S. Pat. No. 5,262,295.

Typical hindered phenols include, but are not limited to, 2,6-di-t-butylphenol, 2,6-di-t-butyl-4-methylphenol, 2,4-di-t-butylphenol, 2,6-dichlorophenol, 2,6-dimethylphenol, and 2-t-butyl-6-methylphenol.

Typical hindered naphthols include, but are not limited to, 1-naphthol, 4-methyl-1-naphthol, 4-methoxy-1-naphthol, 4-chloro-1-naphthol, and compounds described in U.S. Pat. No. 5,262,295.

Moreover, other compounds disclosed as reducing agents include amidoximes (for example, phenylamidoxime), 2-thienylamidoxime, p-phenoxyphenylamidoxime, a combination of an aliphatic carboxylic allyl hydrazide and ascorbic acid (for example, a combination of 2,2'-bis(hydroxymethyl)-propionyl-β-phenyl hydrazide and ascorbic acid), a combination of a polyhydroxybenzene and at least one of hydroxylamine, reductone and hydrazine (for example, a combination of hydroquinone and bis(ethoxyethyl)hydroxylamine), piperidi-4-methylphenylhydrazine, hydroxamic acids (for example, phenylhydroxamic acid, p-hydroxyphenylhydroxamic acid, and o-alaninehydroxamic acid), a combination of an azine and a sulfonamidophenol (for example, a combination of phenothiazine and 2,6-dichloro-4-benzenesulfonamidophenol), α-cyanophenylacetic acid derivatives (for example, ethyl-α-cyano-2-methylphenylacetic acid and ethyl-α-cyanophenylacetic acid), bis-o-naphthol (for example, 2,2'-dihydroxy-1-binaphthyl, 6,6'-dibromo-2,2'-dihydroxy-1,1'-binaphthyl, and bis(2-hydroxy-1-naphthyl) methane), a combination of bis-naphthol and a 1,3-dihydroxybenzene derivative (for example, 2,4-dihydroxybenzophenone and 2,4-dihydroxyacetophenone), 5-pyrazolones (for example, 3-methyl-1-phenyl-5-pyrazolone), reductones (for example, dimethylaminohexose reductone, anhydrodihydro-aminohexose reductone, and anhydrodihydro-piperidone-hexose reductone), indane-1,3-diones (for example, 2-phenylindane-1,3-dione), chromans (for example, 2,2-dimethyl-7-t-butyl-6-hydroxychroman), 1,4-dihydroxypyridines (for example, 2,6-dimethoxy-3,5-dicarbetoxy-1,4-dihydropyridine), ascorbic acid derivatives (1-ascorbic palmitate, ascorbic stearate), unsaturated aldehydes (ketones), and 3-pyrazolidones.

Examples of a reducing agent that can be used in the present invention include substituted hydrazines such as sulfonyl hydrazines described in U.S. Pat. No. 5,464,738. Other useful reducing agents are described, for example, in U.S. Pat. Nos. 3,074,809, 3,094,417, 3,080,254 and 3,887,417. Auxiliary reducing agents descried in U.S. Pat. No. 5,981,151 are also useful.

The reducing agent may be a combination of a hindered phenol reducing agent and a compound selected from various auxiliary reducing agents such as those mentioned below. In addition, a mixture of such a combined agent plus a contrast enhancer (that is, a mixture of the 3 components) is also useful. As such an auxiliary reducing agent, it is possible to use trityl hydrazide and formyl-phenyl hydrazide described in U.S. Pat. No. 5,496,695.

A contrast enhancer may be used in combination with the reducing agent. Useful contrast enhancers include, but are not limited to, hydroxylamines (including hydroxylamine and alkyl- and aryl-substituted derivatives thereof), alkanolamines and phthalic ammonium described in U.S. Pat. No. 5,545,505, hydroxamic acid compounds described in U.S. Pat. No. 5,545,507, N-acylhydrazine compounds described in U.S. Pat. No. 5,558,983, and hydrogen atom donor compounds described in U.S. Pat. No. 5,637,449.

Not all combinations of reducing agents and organic silver salts are equally effective. A preferred combination is a benzotriazole silver salt used as an organic silver salt, a substituted compound thereof or a mixture thereof, with an ascorbic acid reducing agent used as a reducing agent.

The reducing agent of the present invention may be contained in an amount of 1 weight % to 10 weight % (dry weight) based on the amount of silver in organic silver. When the reducing agent is added to a layer other than the layer containing the organic silver salt in a multilayer structure, the amount of the reducing agent is slightly higher, and it is desirably from approximately 2 weight % to approximately 15 weight %. An auxiliary reducing agent is contained in an amount of about 0.001 weight % to 1.5 weight % (dry weight).

10. Other Auxiliary Agents

Other auxiliary agents contained in the amplification solution may include a buffer, an antiseptic such as an antioxidant or an organic stabilizer, and a speed regulator. Examples of a buffer used herein include buffers comprising acetic acid, citric acid, sodium hydroxide, a salt thereof, or tris(hydroxymethyl)aminomethane, and other buffers used in ordinary chemical experiments. Using these buffers as appropriate, the pH of the amplification solution can be adjusted to the optimal pH.

The present invention will be more specifically described in the following examples. However, these examples are not intended to limit the scope of the present invention.

EXAMPLES (1) Preparation of Immunochromatographic Kits for Detection of Influenza Type A or B Viruses (1-1) Preparation of Anti-Influenza Type A or B Antibody-Labeled Gold Colloid (1-1-1) Preparation of Anti-Influenza Type A Antibody-Labeled Gold Colloid 1 mL of a 90 µg/mL anti-influenza type A monoclonal antibody (Anti-Influenza A SPTN-5 7307, Medix Biochemica) solution was added to a gold colloidal solution having pH adjusted by addition of 1 mL of a 50 mM $KH_2PO_4$ buffer (pH 7.5) to 9 mL of a 50-nm diameter gold colloidal solution (EM.GC50, BBI), followed by agitation. The mixture was allowed to stand for 10 minutes and then 550 µL of 1% polyethylene glycol (PEG Mw. 20000, Product No. 168-11285, Wako Pure Chemical Industries, Ltd.) aqueous solution was added to the mixture, followed by agitation. A 10% bovine serum albumin (BSA FractionV, Product No. A-7906, SIGMA) aqueous solution (1.1 mL) was added to the resultant, followed by agitation. The solution was centrifuged at 8000×g and 4° C. for 30 minutes (himacCF16RX, Hitachi). The supernatant was removed so that approximately 1 mL of the solution remained. The gold colloids were dispersed again using an ultrasonic washing machine. Subsequently, the solution was then dispersed in 20 mL of a gold colloidal storage solution (20 mM Tris-HCl buffer (pH 8.2), 0.05% PEG (Mw.20000), 150 mM NaCl, 1% BSA, and 0.1% $NaN_3$) and then centrifuged again at 8000×g and 4° C. for 30 minutes. The supernatant was removed so that approximately 1 mL of the solution remained. The gold colloids were dispersed again using an ultrasonic washing machine, so that an antibody-labeled gold colloid (50 nm) solution was obtained.

(1-1-2) Preparation of Anti-Influenza Type B Antibody-Labeled Gold Colloid 1 mL of a 80 µg/mL anti-influenza type B monoclonal antibody (MONOTOPE aby Influenza B Virus (nuclear) Purified 1131, ViroStat, Inc.) solution was added to a gold colloidal solution having pH adjusted by addition of 1 mL of a 50 mM $KH_2PO_4$ buffer (pH 8.0) to 9 mL of a 50-nm diameter gold colloidal solution (EM.GC50, BBI), followed by agitation. The mixture was allowed to stand for 10 minutes and then 550 µL of 1% polyethylene glycol (PEG Mw. 20000, Product No. 168-11285, Wako Pure Chemical Industries, Ltd.) aqueous solution was added to the mixture, followed by agitation. A 10% bovine serum albumin (BSA FractionV, Product No. A-7906, SIGMA) aqueous solution (1.1 mL) was added to the resultant, followed by agitation. The solution was centrifuged at 8000×g and 4° C. for 30 minutes (himacCF16RX, Hitachi). The supernatant was removed so that approximately 1 mL of the solution remained. The gold colloids were dispersed again using an ultrasonic washing machine. Subsequently, the solution was then dispersed in 20 mL of a gold colloidal storage solution (20 mM Tris-HCl buffer (pH 8.2), 0.05% PEG (Mw.20000), 150 mM NaCl, 1% BSA, and 0.1% $NaN_3$) and then centrifuged again at 8000×g and 4° C. for 30 minutes. The supernatant was removed so that approximately 1 mL of the solution remained. The gold colloids were dispersed again using an ultrasonic washing machine, so that an antibody-labeled gold colloid (50 nm) solution was obtained.

(1-2) Preparation of Gold Colloidal Antibody Holding Pad

The influenza type A or B antibody-labeled gold colloids prepared in (1-1) above were mixed at a ratio of 1:1, and the mixture was diluted with water and a coating solution for a gold colloid (20 mM Tris-Hcl buffer (pH 8.2), 0.05% PEG (Mw. 20000), and 5% sucrose) to set the OD at 520 nm to 3.0.

This solution was uniformly coated to glass fiber pads (Glass Fiber Conjugate Pad, Millipore) cut to the size of 8 mm×150 mm in an amount of 0.8 mL per pad. The pads were dried under reduced pressure overnight to obtain gold colloidal antibody holding pads.

(1-3) Preparation of Antibody-Immobilized Membrane (Chromatographic Carrier)

(1-3-1) Preparation of Antibody-Immobilized Membrane (Chromatographic Carrier) (Line Coating)

An antibody-immobilized membrane was prepared in the following manner by immobilizing an antibody on a nitrocellulose membrane (HiFlow Plus HF120 with a plastic lining, Millipore) cut to the size of 25 mm×200 mm. The membrane, with one of its long sides facing downward, was coated with an anti-influenza type A monoclonal antibody (for immobilization) (Anti-Influenza A SPTN-5 7307, Medix Biochemica) solution prepared at a concentration of 1.5 mg/ml with the use of a coater of inkjet type (BioDot Ltd.). Specifically, the membrane was coated so that a linear portion thereof 7 mm above the lower edge was coated to have a width of approximately 0.7 mm. In a similar manner, the membrane was coated with an anti-influenza type B monoclonal antibody (for immobilization) (MONOTOPE aby Influenza B Virus (nuclear) Purified 1131, ViroStat, Inc.) solution prepared at a concentration of 1.5 mg/ml, so that a linear portion thereof 10 mm above the lower edge was coated to have a width of approximately 0.7 mm. Further, in a similar manner, the membrane was coated with a control anti-mouse IgG antibody (anti-mouse IgG (H+L), rabbit F(ab')2, Product No. 566-70621, Wako Pure Chemical Industries, Ltd.) solution prepared at a concentration of 0.5 mg/ml, so that a linear portion thereof 13 mm above the lower edge was coated. The coated membrane was dried at 50° C. for 30 minutes with a hot-air dryer. The membrane was immersed in ~500 ml of a blocking solution (50 mM borate buffer (pH 8.5) containing 0.5 w % casein (milk-derived product, Product No. 030-01505, Wako Pure Chemical Industries, Ltd.)) in a vat and then allowed to stand therein for 30 minutes. Thereafter, the membrane was transferred to and immersed in 500 ml of a washing-stabilizing solution (50 mM Tris-HCl buffer (pH 7.5) containing 0.5 w % sucrose and 0.05 w % sodium cholate) in a similar vat and then allowed to stand therein for 30 minutes. The membrane was removed from the solution and then dried overnight at room temperature to give an antibody-immobilized membrane.

(1-3-2) Preparation of Antibody-Immobilized Membrane (Chromatographic Carrier) (Dot Coating)

An antibody-immobilized membrane was prepared in the following manner by immobilizing an antibody on a nitrocellulose membrane (HiFlow Plus HF120 with a plastic lining, Millipore) cut to the size of 25 mm×200 mm. The membrane, with one of its long sides facing downward, was coated in dots (0.2 μl each) at 15 mm intervals with an anti-influenza type A monoclonal antibody (for immobilization) (Anti-Influenza A SPTN-5 7307, Medix Biochemica) solution prepared at a concentration of 1.5 mg/ml with the use of a micropipette. Specifically, the membrane was coated so that a linear portion thereof 7 mm above the lower edge was coated. In a similar manner, the membrane was coated in dots (0.2 μl each) at 15 mm intervals with an anti-influenza type B monoclonal antibody (for immobilization) (MONOTOPE aby Influenza B Virus (nuclear) Purified 1131, ViroStat, Inc.) solution prepared at a concentration of 1.5 mg/ml with the use of a micropipette, so that a linear portion thereof 10 mm above the lower edge was coated. Further, in a similar manner, the membrane was coated in dots (0.2 μl each) at 15 mm intervals with a control anti-mouse IgG antibody (anti-mouse IgG (H+L), rabbit F(ab')2, Product No. 566-70621, Wako Pure Chemical Industries, Ltd.) solution prepared at a concentration of 0.5 mg/ml with the use of a micropipette, so that a linear portion thereof 13 mm above the lower edge was coated.

The coated membrane was dried at 50° C. for 30 minutes with a hot-air dryer. The membrane was immersed in 500 ml of a blocking solution (50 mM borate buffer (pH 8.5) containing 0.5 w % casein (milk-derived product, Product No. 030-01505, Wako Pure Chemical Industries, Ltd.)) in a vat and then allowed to stand therein for 30 minutes. Thereafter, the membrane was transferred to and immersed in 500 ml of a washing-stabilizing solution (50 mM Tris-HCl buffer (pH 7.5) containing 0.5 w % sucrose and 0.05 w % sodium cholate) in a similar vat and then allowed to stand therein for 30 minutes. The membrane was removed from the solution and then dried overnight at room temperature to give an antibody-immobilized membrane (dot coating).

(1-4) Preparation of Immunochromatographic Strip

The antibody-immobilized membrane prepared in (1-3) above was adhered to a back pressure-sensitive adhesive sheet (ARcare9020, NIPPN TechnoCluster, Inc.). At this time, the membrane was used with the anti-influenza type A antibody line side (one of the long sides of the membrane) facing downward. The gold colloidal antibody holding pad prepared in (1-2) above was adhered onto the antibody-immobilized membrane such that the pad overlapped the lower portion of the antibody-immobilized membrane by approximately 2 mm. The sample addition pad (glass fiber pad (Glass Fiber Conjugate Pad, Millipore) cut to the size of 18 mm×150 mm was adhered to the gold colloidal antibody holding pad such that the sample addition pad overlapped the lower portion of the gold colloidal antibody holding pad by approximately 4 mm. Further, an absorbent pad (cellulose/glass membrane cut to the size of 80 mm×150 mm (CF6, Whatman)) was adhered onto the antibody-immobilized membrane such that the absorbent pad overlapped the upper portion of the antibody-immobilized membrane by approximately 5 mm.

With the use of a guillotine cutter (CM4000, NIPPN TechnoCluster, Inc.), the thus overlapped and adhered members (immunochromatographic kit members) were cut in parallel to the short sides of the overlapped members at 15-mm intervals on the long sides thereof, whereby 15 mm×55 mm immunochromatographic strips were prepared. These strips were used as immunochromatographic kits for testing.

When an immunochromatographic strip was prepared with a dot-coated membrane prepared in (1-3-2), the cutting position on the membrane was adjusted in a manner such that the site on which antibodies had been added dropwise was positioned at the center of a prepared immunochromatographic kit for testing.

(1-5) Preparation of Immunochromatographic Kit Containing a Pad Used for Developing a Liquid from the Side Thereof (Used in Comparative Example 1)

The position of the center point between both edges of a strip (immunochromatography kit for testing prepared in (1-4) in an area between two capture sites (TL) on the strip was determined on the assumption that a straight line connecting an amplification solution addition pad and a water absorbent pad would overlap the center point. In addition, the angle formed by a line extending in the direction of development of an amplification solution and a line extending in the direction of development of a specimen solution was determined to be 45°, 60°, 90°, 135°, 150°, or 170°. Under the above conditions, an amplification solution addition pad (a glass fiber pad cut to a size of 18 mm×8 mm (Glass Fiber Conjugate Pad, Millipore) onto which a back pressure-sensitive adhesive sheet with a size of 13 mm×8 mm (ARcare9020, NIPPN TechnoCluster, Inc.) had been adhered) was attached with tape to the upstream end (for development of an amplification solution) of the strip. A water absorbent pad (a cellulose membrane cut to a size of 100 mm×8 mm (CF6, Whatman) onto which a back pressure-sensitive adhesive sheet cut to a size of 95 mm×8 mm (ARcare9020, NIPPN TechnoCluster, Inc.) had been adhered) was attached to the downstream end (for development of an amplification solution) of the strip.

(1-6) Wash Solution

A PBS buffer containing 1% BSA obtained by dissolving BSA (1% by weight, SIGMA) in a PBS buffer (Wako Pure Chemical Industries, Ltd.) was used as a wash solution.

(1-7) Preparation of Silver Amplification Solution (1-7-1) Preparation of Amplification Solution A (1-7-1-1) Preparation of Amplification Solution A-1

1 mol/L iron nitrate aqueous solution (40 mL) prepared by dissolving iron (III) nitrate enneahydrate (Wako Pure Chemical Industries, Ltd., 095-00995) in water, citric acid (10.5 g) (Wako Pure Chemical Industries, Ltd., 038-06925), dodecylamine (0.1 g) (Wako Pure Chemical Industries, Ltd., 123-00246), and a surfactant (0.44 g) ($C_9H_{19}$—$C_6H_4$—O—($CH_2CH_2O$)$_{50}$H) were dissolved in water (325 g). After completion of dissolution, nitric acid (40 mL, 10% by weight) was added to the solution while the solution was stirred with a stirrer. A portion (80 mL) of the resulting solution was measured. Iron (II) ammonium sulfate hexahydrate (11.76 g) (Wako Pure Chemical Industries, Ltd., 091-00855) was added thereto. Thus, an amplification solution A-1 was prepared.

(1-7-1-2) Preparation of Amplification Solution A-2

Water was added to a silver nitrate solution (10 mL) (containing silver nitrate (10 g)) to a total volume of 100 g. Thus, an amplification solution A-2 (a silver nitrate aqueous solution (10% by weight)) was prepared.

(1-7-1-3) Preparation of an Amplification Solution A

A portion (40 mL) of an amplification solution A-1 was measured. An amplification solution A-2 (4.25 mL) was added thereto, followed by stirring. Thus, an amplification solution A was prepared.

(2) Evaluation

Comparative Example 1

(2-0) Setting of a Device

A wash solution addition pad (a second insoluble carrier) (a glass fiber pad cut to a size of 18 mm×8 mm (Glass Fiber Conjugate Pad, Millipore) onto which a back pressure-sensitive adhesive sheet with a size of 13 mm×8 mm (ARcare9020, NIPPN TechnoCluster, Inc.) had been adhered) was attached with tape to an immunochromatographic strip (a first insoluble carrier) prepared in (1-4). A water absorbent pad (a cellulose membrane cut to a size of 25 mm×8 mm (CF6, Whatman) onto which a back pressure-sensitive adhesive sheet in a size of 20 mm×8 mm (ARcare9020, NIPPN TechnoCluster, Inc.) had been adhered) was attached to the downstream end of the strip.

A wash solution (500 μL) prepared in (1-6) was introduced into a liquid storage pot. The immunochromatographic strip prepared above, onto which a wash solution addition pad and a water absorbent pad had been adhered, was placed in a manner such that the strip did not come into contact with the wash solution. Then, the pot was closed with its upper lid.

(2-1) Dropwise Introduction and Development of an Antigen Solution

A "SEIKEN" quick S-Influ A-B negative/positive control (product no. 322968, DENKA SEIKEN Co., Ltd.) was used as a specimen solution. The detection limit obtained with the use of a commercially available "Capilia FluA•B" immunochromatography detection kit (Alfresa Pharma Corporation) was ¹⁄₄₀ for a solution obtained by diluting the positive control solution (A•B) with a PBS buffer containing BSA (1% by mass). Herein, the positive control was ¹⁄₂₀₀ diluted with a PBS buffer containing BSA (1% by mass). The resultant was used as a specimen solution.

The specimen solution was introduced dropwise into pores 5 for dropwise introduction of an analyte of an immunochromatography kit for testing prepared in (1-4) in a manner such that each pore contained 300 μL of the specimen solution. The specimen solution was allowed to stand for 10 minutes. In such case, the concentration was below the concentration at the detection limit (¹⁄₄₀-diluted solution for the above kit) and thus it was impossible to visually confirm the detection line.

(2-2) Washing and Signal Amplification with the Use of Amplification Solution

After development of an antigen solution for 10 minutes, the edge of the wash solution addition pad was pushed with a stick so that it was immersed in the wash solution in the liquid storage pot. The wash solution was developed on the strip for washing for 5 minutes.

The remaining wash solution was removed from the liquid storage pot. Then, an amplification solution A (500 μL) prepared in (1-7) was introduced into the pot. The edge of the wash solution addition pad was pushed with a stick so that it was immersed in the liquid amplification solution in the storage pot for development of the solution. 2 minutes thereafter, the membrane was removed therefrom, followed by water washing for 3 minutes.

(2-3) Sensitivity Evaluation

After amplification, the reflection absorption of the detection line was measured using an ICA-1000 (Hamamatsu Photonics K.K.). An absorbance difference (ΔOD) between the background and the line was determined and evaluated (note that the ΔOD value is proportional to the degree of ease of visual observation, and most people can visually confirm a line at a value of 5 mABS or more). The experiment was repeated twice. The average of the results was obtained. Table 1 shows the results.

Example 1

(2-4) Setting of a Device

The experiment was conducted using the device shown in FIG. 1.

A wash solution addition pad 3 (a second insoluble carrier) (a glass fiber pad cut to a size of 18 mm×8 mm (Glass Fiber Conjugate Pad, Millipore) onto which a back pressure-sensitive adhesive sheet with a size of 13 mm×8 mm (ARcare9020, NIPPN TechnoCluster, Inc.) had been adhered) and a water absorbent pad 4 (a third insoluble carrier) (a cellulose membrane cut to a size of 25 mm×8 mm (CF6, Whatman) onto which a back pressure-sensitive adhesive sheet with a size of 20 mm×8 mm (ARcare9020, NIPPN TechnoCluster, Inc.) had been adhered) were attached to a second device part 6 shown in FIG. 1.

An immunochromatographic strip (a first insoluble carrier) 1 prepared in (1-4) was attached to a first device part 5.

(2-5) Dropwise Introduction and Development of Antigen Solution

Dropwise introduction and development of an antigen solution were carried out as in the case of (2-1).

(2-6) Washing and Signal Amplification with the Use of Amplification Solution

After development of an antigen solution for 10 minutes, a wash solution (500 μL) prepared in (1-6) was introduced into a liquid storage pot 2 in the device shown in FIG. 1. A second device part 6 was connected to a first device part 5 such that the edge of the wash solution addition pad was immersed in the wash solution in the liquid storage pot, and such that the wash solution addition pad (a second insoluble carrier) 3 and a water absorbent pad (a third insoluble carrier) 4 were attached to the side of the immunochromatographic strip. Accordingly, the wash solution was developed on the strip for washing for 5 minutes.

The remaining wash solution was removed from the liquid storage pot 2. An amplification solution A (500 μL) prepared in (1-7) was introduced into the pot. The edge of the wash solution addition pad 2 was pushed with a stick so that it was immersed in the amplification solution in the liquid storage pot such that the solution was developed on the pad. 2 minutes thereafter, the membrane (pad) was removed therefrom, followed by water washing for 3 minutes.

(2-7) Background Evaluation and Sensitivity Evaluation

Background evaluation and sensitivity evaluation were carried out as in the case of (2-3). Table 1 shows the results.

Example 2

Example 2 was carried out as in Example 1, provided that a membrane coated with an antibody in dots in (1-3-2) was used as an immunochromatographic strip.

The background detection point was the midpoint of two capture sites.

Table 1 shows sensitivity evaluation results.

Example 3

(2-8) Setting of a Device

Figure 2:
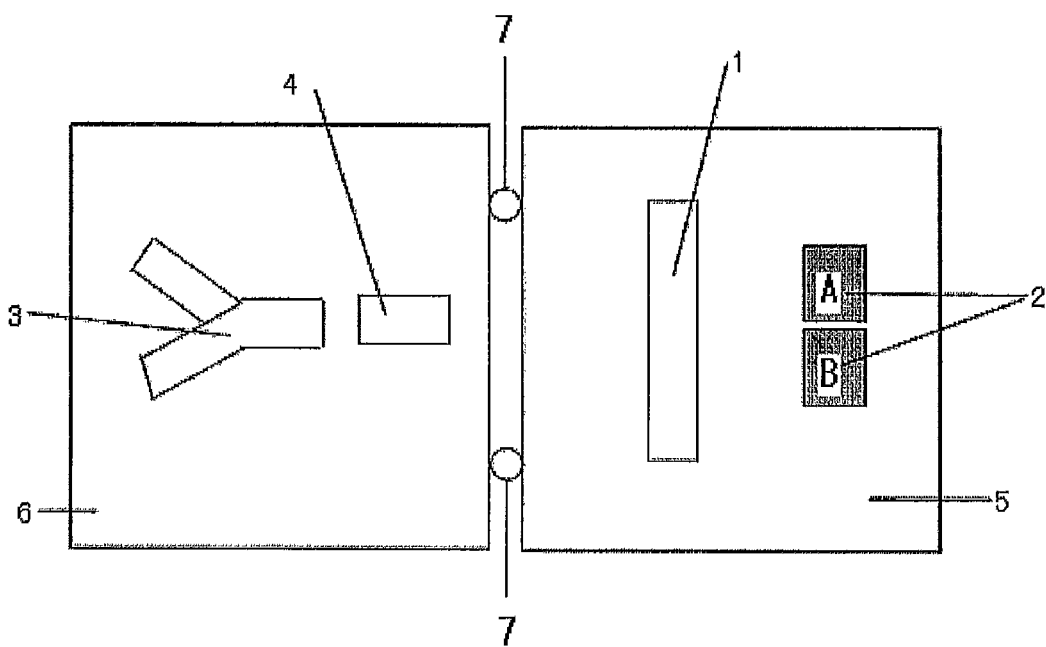
FIG. 2 shows another example of the immunochromatographic device of the present invention.
Figure 3:
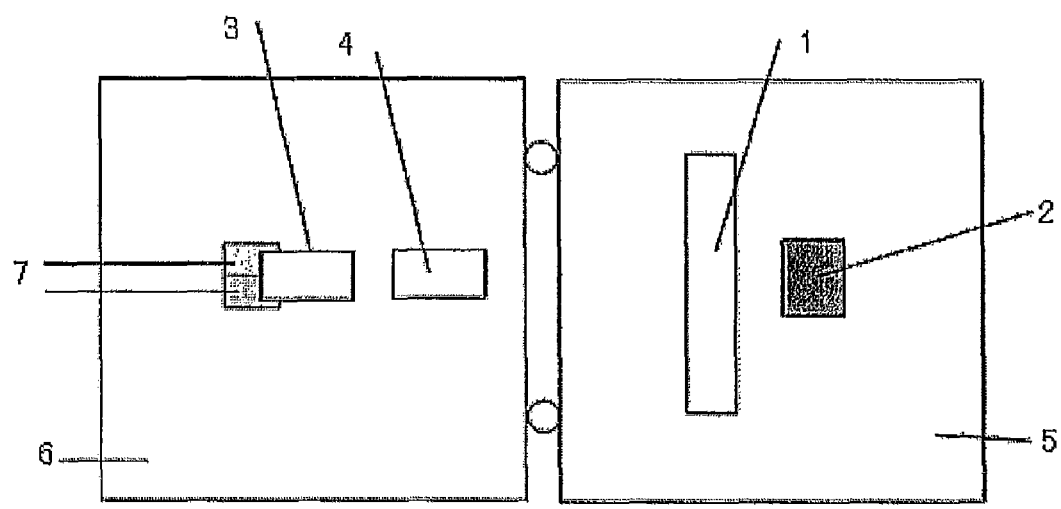
FIG. 3 shows another example of the immunochromatographic device of the present invention.
Figure 4:
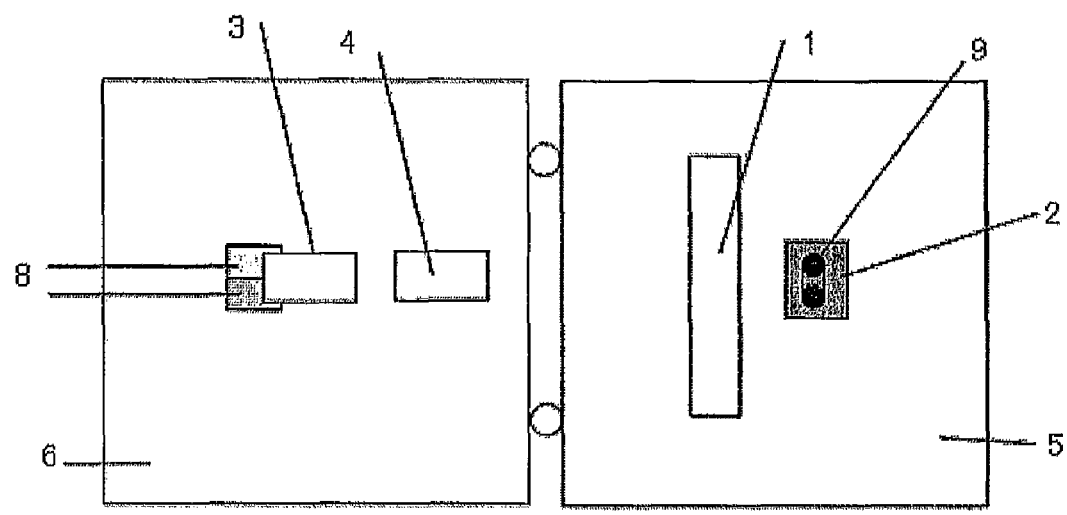
FIG. 4 shows another example of the immunochromatographic device of the present invention.

As shown in FIG. 2, a device containing two separate liquid storage pots (liquid storage pots A and B) was used. A two-way split glass fiber pad 3 (Glass Fiber Conjugate Pad, Millipore) as shown in FIG. 2 was used as a second insoluble carrier 3. As shown in FIG. 2, a glass fiber pad 3 that had been partially coated with a 5% BSA solution was used.

Regarding conditions other than the above conditions, setting of the device was carried out as in Example 1.

(2-9) Dropwise Introduction and Development of an Antigen Solution

Dropwise introduction and development of an antigen solution was carried out as in the case of (2-1).

(2-10) Washing and Signal Amplification with the Use of an Amplification Solution After development of an antigen solution for 10 minutes, an amplification solution A-1 (500 μL) prepared in (1-6-1-1) was introduced into a liquid storage pot A in a device shown in FIG. 2, and an amplification solution A-2 (500 μL) prepared in (1-6-1-2) was introduced into a liquid storage pot B in a device shown in FIG. 2. A second device part 6 was connected to a first device part 5 such that one end of a two-way split membrane was immersed in the liquid storage pot A and the other end of the two-way split membrane was immersed in the liquid storage pot B, and such that the two-way split membrane (the second insoluble carrier) 3 and a water absorbent pad (the third insoluble carrier) 4 were attached to the side of the immunochromatographic strip. In the above case, the amplification solution A-1 was first added to one end of the two-way split membrane, following which the amplification solution A-2 was added to the other end of the two-way split membrane. Then, washing and amplification were carried out. 5 minutes thereafter, the membrane was removed therefrom, followed by water washing for 3 minutes.

Table 1 shows sensitivity evaluation results.

Example 4

Example 4 was carried out as in Example 3, provided that an amplification solution A-1 (500 μL) prepared in (1-6-1-1) was introduced into a liquid storage pot A and an amplification solution A-2 (500 μL) prepared in (1-6-1-2) was introduced into a liquid storage pot B. In addition, the pots were sealed with aluminium foil and tape such that the pots containing liquid inside thereof became portable.

When a second device part 6 was connected to a first device part 5, the seal with aluminium foil was opened such that liquid feeding was initiated.

Regarding conditions other than the above conditions, the experiment was carried out as in Example 3.

Table 1 shows sensitivity evaluation results.

TABLE 1

| | Line concentration after amplification (ΔOD) |
|---|---|
| Before amplification | 0.000 |
| Comparative Example 1 | No line detected |
| Example 1 | 0.035 |
| Example 2 | 0.039 |
| Example 3 | 0.024 |
| Example 4 | 0.021 |

The invention claimed is:

1. An immunochromatographic device, which contains the following (a) and (b):
    (a) a first device part holding a first insoluble carrier used for developing a complex formed with an analyte and a labeling substance comprising a metal labeled with a first binding substance that can bind to the analyte and used for capturing the analyte and the labeling substance, wherein the first insoluble carrier includes a sample-adding pad, a labeling substance-retaining pad containing the labeling substance therein or thereon, a chromatographic carrier containing at a reaction portion a second binding substance that can bind to the analyte, and an absorbent pad in this order from the upstream to the downstream of the development direction; and
    (b) a second device part holding a second insoluble carrier used for developing a liquid and a third insoluble carrier used for absorbing a liquid,
    wherein the first device part (a) and the second device part (b) are contained in the immunochromatographic device in a state where the first insoluble carrier is not in contact with the second insoluble carrier and the third insoluble carrier, and
    the first device part has a liquid storage pot.

2. The immunochromatographic device according to claim 1, which further comprises a positioning mechanism whereby the positions of the first device part and the second device part can be positioned in a manner such that the first insoluble carrier comes into contact or does not come into contact with the second insoluble carrier and the third insoluble carrier.

3. The immunochromatographic device according to claim 1, wherein the second device part has pores for dropwise introduction of an analyte.

4. The immunochromatographic device according to claim 1, which has a structure in which one end of the second insoluble carrier is immersed in the liquid storage pot when the first device part and the second device part are positioned in a manner such that the first insoluble carrier comes into contact with the second insoluble carrier and the third insoluble carrier.

5. The immunochromatographic device according to claim 1, wherein the liquid storage pot is previously loaded with a liquid.

6. The immunochromatographic device according to claim 1, which has a structure in which the first device part has two liquid storage pots and one end of the second insoluble carrier is split in two ways,
provided that the two split ends are separately immersed in the two liquid storage pots when the first device part and the second device part are positioned in a manner such that the first insoluble carrier comes into contact with the second insoluble carrier and the third insoluble carrier.

7. The immunochromatographic device according to claim 1, wherein the first device part has a first liquid storage pot, the second device part has two second liquid storage pots positioned to face the first liquid pot, and a silver-containing compound and a reducing agent for silver ion are separately and previously loaded into the two second liquid storage pots.

8. The immunochromatographic device according to claim 1, wherein the first device part has a first liquid storage pot, the second device part has two second liquid storage pots positioned to face the first liquid pot, and the first liquid storage pot has inside a Y- or V-shaped projecting pin facing the second liquid storage pots,
provided that the external wall of each second liquid storage pot is pierced with the projecting pin and thus liquids inside the two second liquid storage pots are transferred via the projecting pin into the first liquid storage pot, followed by mixing, when the first device part and the second device part are positioned in a manner such that the first insoluble carrier comes into contact with the second insoluble carrier and the third insoluble carrier.

9. The immunochromatographic device according to claim 1, wherein the first insoluble carrier is a porous carrier.

* * * * *